United States Patent [19]
Wada et al.

[11] Patent Number: 5,833,733
[45] Date of Patent: *Nov. 10, 1998

[54] AGROCHEMICAL FORMULATIONS FOR WATER SURFACE APPLICATION

[75] Inventors: Yuzuru Wada, Hachioji; Yasuhiro Kamada; Katsuhiko Hanaki, both of Oyama, all of Japan

[73] Assignee: Nihon Bayer Agrochem K.K., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 642,976

[22] Filed: May 6, 1996

[30] Foreign Application Priority Data

May 12, 1995 [JP] Japan .................................. 7-137478

[51] Int. Cl.$^6$ ............................ A01N 25/08; A01N 25/30
[52] U.S. Cl. .............................. 71/27; 71/31; 71/64.02; 71/64.11; 71/904; 504/101; 504/116
[58] Field of Search ................... 71/27, 64.02, 64.07, 71/64.11, 64.13, 904, 31; 504/101, 116

[56] References Cited

PUBLICATIONS

Derwent Abstract, Accension No. 92–320859/39, Abstract of JP 04226901, (1992).
Derwent Abstract, Accension No. 93–140273/17, Abstract of JP 05078204, (1993).
Derwent Abstract, Accension No. 93–278151/35, Abstract of JP 05194105, (1993).
Derwent Abstract, Accension No. 94–354575/44, Abstract of JP 06279204, (1994).

Primary Examiner—Gary P. Straub
Attorney, Agent, or Firm—Sprung Kramer Schaefer & Briscoe

[57] ABSTRACT

New agrochemical formulations for application to the water of paddy fields, which formulations comprise A) at least one solid core material having an apparent specific density of less than 1 and a particle diameter within the range from about 300 μm to about 1,400 μm, and B) a coating layer comprising
  at least one biologically active compound,
  at least one substance having the ability to reduce the interfacial tension between water and air,
  at least one oily substance and,
  if appropriate, one or more additives, and the use of such agrochemical formulations for applying biologically active compounds to the water of paddy fields.

12 Claims, 1 Drawing Sheet

AGROCHEMICAL FORMULATIONS FOR WATER SURFACE APPLICATION

The present invention relates to new agrochemical formulations, which are applied to the surface of water where they float and drift along. More specifically, the invention relates to new agricultural formulations in solid form and to their use for spreading chemicals on the surface of water in paddy fields.

Various types of formulations have already been known in order to spread chemicals for use in agriculture. Thus, agricultural chemicals can be applied in the form of formulations, such as granules, powders, wettable powders, flowable agents, aqueous solutions, liquids, emulsions, etc. Furthermore, there have recently been developed tablets and packs, i.e. synthetic materials in solid form impregnated with the active compounds.

It has also been required in the agricultural field to improve the form of the formulations of chemicals to be used in agriculture, since the demand for further labour-saving is increasing, the amount of the agrochemicals to be applied has to be minimized due to consideration of environmental aspects, etc.

Under such circumstances, it has been developed in recent years to reduce the dosage of granules from an amount of 30 kg/ha to 10 kg/ha, to spread formulations by means of machines and to use large-sized throw-in formulations. By using large-sized throw-in formulations, it is intended to uniformly disperse the effective components in the water of paddy fields. For this purpose, said formulations are thrown into the water from a footpath, but not from within the paddy field by an operator, who entered the water. Specifically, there have been tested tablets, balls and separate packages of 100 g or 50 g, from which the effective components are intended to be easily dispersed from the surface of the water of paddy fields by means of water-soluble excipients and foaming agents. However, these fomulations are applied in an extremely localized point as compared with conventional granules. Accordingly, it takes a longer period of time for the active ingredients of the formulations to be uniformly dispersed from the surface of water of the paddy field, or in some cases, the effective components are not being dispersed on the entire surface of water of the paddy field. As a result thereof, their effects become uneven or phytotoxicity is observed.

At risk of repetition, the large-sized throw-in formulations are suitable to save the labour-costs of the application. However, they suffer from the disadvantage that it is difficult to speedily and uniformly disperse the effective components of the preparations from the surface of the water of the paddy fields. Thus, it has been required to prepare formulations not having this disadvantage.

As a result of extensive research to resolve the above-mentioned problem, there have been found now new agricultural formulations for the treatment of the water surface of paddy fields. Upon applying said formulations to the water surface, they float and drift along on the water surface, whereby it is achieved to uniformly disperse the biologically active substances from the entire water surface of the paddy field.

Thus, the present invention provides new agrochemical formulations in the form of solid particles, which are composed of A) at least one solid core material having an apparent specific density of less than 1 and a particle diameter within the range from about 300 $\mu$m to about 1,400 $\mu$m, and B) a coating layer comprising
   at least one biologically active compound,
   at least one substance having the ability to reduce the interfacial tension between water and air,
   at least one oily substance and,
   if appropriate, one or more additives.

The present invention further provides a process for the preparation of agrochemical formulations, which process consists in a) adding at least one oily substance to at least one solid core material having an apparent specific density of less than 1 and a particle diameter within the range from about 300 $\mu$m to about 1,400 $\mu$m, and b) coating the pre-treated core material with a mixture comprising
   at least one biologically active compound,
   at least one substance having the ability to reduce the interfacial tension between water and air and,
   if appropriate, one or more additives.

After all, the present invention provides a method for applying agrochemicals to the water of paddy fields, which method consists in adding to the water surface of paddy fields formulations in the form of solid particles, which are composed of A) at least one solid core material having an apparent specific density of less than 1 and a particle diameter within the range from about 300 $\mu$m to about 1,400 $\mu$m, and B) a coating layer comprising
   at least one biologically active compound,
   at least one substance having the ability to reduce the interfacial tension between water and air,
   at least one oily substance and,
   if appropriate, one or more additives.

The apparent specific density, in the present context, is understood as being the value calculated by dividing the mass (g) of one particle having internal voids by the volume (ccm) of one particle having internal voids. This value is different from the bulk specific density.

It is decidedly surprising that the agrochemical formulations according to the invention are better suitable for uniformly dispersing biologically active compounds in the water of paddy fields than corresponding known preparations.

The agrochemical formulations according to the invention are distinguished by a series of advantages. Thus, upon applying said formulations to the water of paddy fields, the particles float and drift along in random directions on the water surface. As a result thereof, the particles are extremely speedily and uniformly spread over the entire water surface, and due to the drifting of the particles, the biologically active compounds are released from the particles and are uniformly dispersed in the water of the paddy field. A further particular advantage of the new agrochemical formulations is that they do not exert any negative effects, such as phytotoxicity. After all, it should be pointed out that the efficacy of the biologically active compounds is fully maintained, even if the particles of the core material remain on the surface of the water and are blown together by the wind, since the active compounds have already been dispersed because of their very high releasing rate.

A detailed description of the agrochemical formulations according to the invention, the process for their preparation and of the method of their use is given in the following.

The particles of the core material serve as carriers of the agrochemicals according to the invention. As core materials, the formulations can contain any customary carriers in the form of particles having an apparent specific density of less than 1 and a particle diameter within the range from about 300 μm to about 1,400 μm, preferably from about 500 μm about 1,400 μm. Core materials in the form of particles having such a diameter can be prepared by using a standard sieve according to the Japanese Industrial Standard (JIS) and by removing larger particles than the upper limit of the above range and by removing smaller particles than the lower limit.

Suitable carriers are for example materials in the form of particles selected from the group comprising pumice, calcined perlite, processed shirasu (trade name Shirasu Ballon), calcined obsidian, calcined pumice and vermiculite. Particularly preferred is processed shirasu.

The core material may consist of one individual carrier or of a mixture of two or more different carriers.

The agrochemical formulations according to the invention comprise one or more biologically active compounds. These are to be understood as meaning all customary substances, which can be used for treating plants in paddy fields. Biologically active compounds in this context are insecticidal compounds, nematocidal compounds, fungicidal compounds, herbicidal compounds, plant nutritive substances, plant growth regulants etc.

The following compounds may be mentioned as examples of biologically active compounds, which can be present in the formulations according to the invention:

2-benzothiazol-2-yloxy-N-methylacetanilide,
2-isopropoxyphenyl-N-methylcarbamate,
1-(6-chloro-3-pyridylmethyl)-N-nitro-imidazolidin-2-ylideneamine,
O,O-dimethyl-O-[3-methyl-4-(methylthio)-phenyl]-thiophosphate,
1-(4-chlorophenoxy)-3,3-dimethyl-1-(1,2,4- triazol-1-yl)-2-butanone,
all-rac-1-(biphenyl-4-yloxy)-3,3-dimethyl-1- (1H-1,2,4-triazol-1-yl)-butan-2-ol,
zinc propylenebisdithiocarbamate,
(RS)-2-bromo-N-(α,α-dimethylbenzyl)-3,3- dimethyl-butyramide,
2-chloro-2',6'-diethyl-N-(2-propoxyethyl)- acetanilide,
2-chloro-2',6'-diethyl-N-(2-butoxymethyl)- acetanilide,
2-chloro-N-(3-methoxy-2-thenyl)-2',6'-dimethylacetanilide,
S-(4-chlorobenzyl)-N,N-diethylthiocarbamate,
S-benzyl 1,2-dimethylpropyl(ethyl)thio- carbamate,
O-3-tert-butylphenyl 6-methoxy-2-pyridyl- (methyl) thiocarbamate,
S-ethylhexamido- 1H-azepin- 1-carbothioate,
1-(diethylcarbamoyl)-3-(2,4,6-trimethyl-phenyl- sulfonyl)-1,2,4-thiazole,
1-(3-chloro-4-trifluoromethylphenyl)-4-(N,N-dimethylcarbamoyl)-5(4H)-tetrazolinone,
1-(3-chloro-4-trifluoromethylthio-phenyl)-4-(N,N-dipropyl carbamoyl)-5(4H)-tetrazolinone,
1-(3-chloro-4-trifluoromethoxy-phenyl)-4-(N,N-dipropylcarbamoyl)-5(4H)-tetrazolinone,
1-(3-chloro-4-isopropylphenyl)-4-(N,N-diethyl-carbamoyl)-5(4H)-tetrazolinone,
1-(3-chloro-4-isopropylphenyl)-4-(N,N-dipropylcarbamoyl)-5(4H)-tetrazolinone,
1-(3-chloro-4-isopropylphenyl)-4-(N,N-diallyl-carbamoyl)-5(4H)-tetrazolinone,
1-(2-chlorophenyl)-4-(N,N-diethylcarbamoyl)-5(4H)-tetrazolinone,
1-(2-chlorophenyl)-4-(N,N-dipropylcarbamoyl)-5(4H)-tetrazolinone,
1-(2-chloro-6-methylphenyl)-4-(N,N-diethyl-carbamoyl)-5(4H)-tetrazolinone,
1-(2,6-dichlorophenyl)-4-(N,N-diethylcarbamoyl)-5(4H)-tetrazolinone,
1-(2-chloro-6-methylphenyl)-4-(N-ethyl-N-iso-propyl)-5(4H)-tetrazolinone,
1-(2-chloro-6-methylphenyl)-4-(N,N-dipropyl-carbamoyl)-5(4H)-tetrazolinone,
1-(2-chlorophenyl)-4-(N-cyclopentyl-N-ethyl-carbamoyl)-5(4H)-tetrazolinone,
1-(2-chlorophenyl)-4-(N-cyclopentyl-N-propyl-carbamoyl)-5(4H)-tetrazolinone,
1-(2-chlorophenyl)-4-(N-cyclohexyl-N-ethyl-carbamoyl)-5(4H)-tetrazolinone,
1-(2-chloro-6-methylphenyl)-4-(N-cyclopentyl-N-propylcarbamoyl)-5(4H)-tetrazolinone,
1-(2-bromophenyl)-4-(N-cyclopentyl-N-ethyl- carbamoyl)-5(4H)-tetrazolinone,
1-(2-bromophenyl)-4-(N-cyclopentyl-N-propyl- carbamoyl)-5(4H)-tetrazolinone,
1-(2-bromo-6-methylphenyl)-4-(N-cyclopentyl-N-propyl carbamoyl)-5(4H)-tetrazolinone,
methyl 2-[(4,6-dimethoxy-2-pyrimidinyl)-oxy]- 6-[1-(methoxyimino)-ethyl]-benzoate,
methyl α-(4,6-dimethoxypyrimidin-2-ylcarbamoylsulfamoyl)-O-toluate,
ethyl-5-(4,6-dimethoxypyrimidin-2-yl-carbamoylsulfamoyl)- 1-methylpyrazol-4-carboxylate,
N-(2-chloroimidazol [1,2-a]pyridin-3-yl -sulfonyl)-N'-(4,6-dimethoxy-2-pyrimidyl)-urea,
N-((4,6-dimethoxypyrimidin-2-yl)-aminocarbonyl)-1-methyl-4-(2-methyl-2H-tetrazol-5-ylk)-1H-pyrazol-5-sulfonamide,
N-[[4,6-dimethoxy- 1,3,5-triazin-2-yl)-amino]-carbonyl]-2-(2-methoxyethoxy)-benzenesulfonamide,
1-[[o-(cyclopropylcarbonyl)phenyl]-sulfamoyl-3-(4,6-dimethoxy-2-pyrimidinyl)-urea,
4-(2,4-dichlorobenzoyl)-1,3-dimethylpyrazol-5-yl-p-toluenesulfonate,
2-[4-(2,4-dichloro-m-toluyl)-1,3-dimethyl-pyrazol-5-yloxy] -4-methy]acetophenone,
2-[4-(2,4-dichlorobenzoyl)-1,3-dimethylpyrazol-5-yloxy]-acetophenone,
2-(β-naphthyloxy)-propionanilide,
(RS)-2-(2,4-dichloro-m-tolyloxy)-propion-anilide,
n-butyl (R)-2-[4-(2-fluoro-4-cyanophenoxy)-phenoxy]-propionate,
1-(α,α-dimethylbenzyl)-3-p-tolylurea,
N- [(2-chlorophenyl)-methyl]-N'-( 1-methyl-1-phenylethyl) -urea,
2-methyl-4-chlorophenoxybutyric acid,
2,4-dichlorophenoxyacetic acid,
2,4-bis-(ethylamino)-6-methylthio-1,3,5-triazine,
2-ethylamino-4-( 1,2-dimethylpropylamino)-6- methylthio-1,3,5-triazine.

The agrochemical formulations according to the invention comprise one or more substances having the ability to reduce the interfacial tension between water and air. Preferred are substances of this type, which can reduce the surface tension of water by 30% or more when added to water at its critical micelle concentration (cmc). As examples of such substances, there may be mentioned the following compounds:

alkylbenzenesulfonates, alkylsulfates, alkylnaphthalenesulfonates, alkylphosphoric esters, polyoxyethylene alkyl ethers, glycerin fatty acid esters, sorbitan fatty acid esters, dialkylsulfosuccinates, ligninsulfonate, condensates of naphthalenesulfonate and formalin, alkylammonium salts, alkylamine salts, alkyliglycine salts, alanine salts, silicon-polyether surfactancts, alkylallylsulfonates, camphor, etc., but the substances are not restricted to them.

Among them, particularly preferred are alkylsulfates, alkylnaphthalenesulfonates, alkylbenzene-sulfonates, dialkylsulfosuccinates and ligninsulfonate. It is desirable that they are generally in a form of a solid powder at a room temperature.

The agrochemical formulations according to the invention also comprise one or more oily substances. Preferred are substances selected from the group comprising paraffin, glycerinesters, fats and oils of animals or plants, and spindle oil. Particularly preferred is spindle oil.

Further, the agrochemical formulations according to the invention may also contain one or more agriculturally acceptable additives selected from extenders, stabilizers and colorants.

The concentrations of the components in the agrochemical formulations according to the invention can be varied within a relatively wide range. In general, the formulations comprise per 100 parts by weight of the formulation from about 0.05 to about 50 parts by weight, preferably from about 1.0 to about 30 parts by weight of one or more biologically active compounds, from about 0.5 to about 25 parts by weight, preferably from about 5 to about 15 parts by weight of one or more substances having the ability to reduce the interfacial tension between water and air, from about 1 to about 30 parts by weight, preferably from about 5 to about 25 parts by weight of one or more oily substances, from about 10 to about 80 parts by weight, preferably from about 10 to about 70 parts by weight of solid core material and if appropriate, from 0 to about 25 parts by weight, preferably from 0 to about 15 parts by weight of one or more additives.

The process for preparing the formulations according to the invention is generally carried out by intimately mixing the solid core material with at least one oily substance in a coating apparatus, preparing a powder by mixing and/or grinding at least one biologically active compound, at least one substance having the ability to reduce the interfacial tension between water and air and, if appropriate, one or more additives in a mixer or grinding-mill, gradually adding the above-mentioned mixture of core material and oily substance whilst stirring in a coating apparatus and continuing the coating process until the surface of the core particles is uniformly covered with powder.

When carrying out the process according to the invention, the temperature can be varied within a certain range. In general, the process is carried out at a temperature between 0° C. and 60° C., preferably between 10° C. and 40° C.

All mixers, grinding-mills and coating apparatuses conventionally suitable for such purposes can be employed for carrying out the process according to the invention. The use of a pin mill and of a pan coater is preferred.

In order to increase the efficiency upon applying the agrochemical formulations according to the invention to the water surface of paddy fields, the agrochemical formulations can be packed in water-soluble bags in units of about 10 g to about 200 g, preferably of about 25 g to about 60 g per package.

As examples of film-forming materials, which are required to prepare the water-soluble bags, there may be mentioned water-soluble poly(vinyl alcohol), carboxymethyl cellulose, dextrin, starch, hydroxyethyl cellulose, and others.

Furthermore, the formulations according to the invention may be placed in certain molds in units of about 10 g to about 200 g. They can be heated and/or compressed so that they are converted into large-sized and molded pieces. Their figures may be that of globes, discs, cylinders, rectangular cubes, pipes, etc. However, the figures are not restricted to the afore-mentioned ones.

For molding, the following binding agents may be used: polyethylene glycol, saccharides, natural gum, poly(vinyl alcohol), natural rubber and synthetic rubber. However, the binding agents are not restricted to the afore-mentioned ones.

The core material for preparing the formulations according to the invention is obtained by screening the solid particles with sieves, which are similar to standard sieves and have openings of a diameter of 1,400 μm and 300 μm or 500 μm respectively.

The formulations according to the invention can be used for various purposes depending on the biologically active ingredients which are contained.

The amounts in which the formulations according to the invention are applied to paddy fields can be varied within a substantial range depending on the kind and degree of activity of the active ingredients in the formulations.

The formulations according to the invention are applied to paddy fields by conventional methods.

The invention is illustrated by the following examples, but is not limited to these examples in any way.

The following biologically active compounds were used in the Examples described below:

Compound A: 2-benzothiazol-2-yloxy-N-methylacetanilide

Compound B: 1-(2-chloro-phenyl)-4-(N-cyclohexyl-N-ethylcarbamoyl)5(4H)-tetrazolinone

EXAMPLES FOR THE PREPARATION OF FORMULATIONS

Example 1

The compounds and quantities used were as follows:

| | |
|---|---|
| Compound A | 10.0% by weight |
| Alkylsulfate | 2.0% by weight |
| Ligninsulfonate | 3.0% by weight |
| Spindle oil | 14.0% by weight |
| Shirasu Ballon | 71.0% by weight |

In order to adjust the particle size of the core material, Shirasu Ballon was screened with sieves, which were similar to Japanese Industrial Standard sieves and hat openings of a diameter of 500 μm and 1,400 μm respectively.

The above-mentioned amounts of Compound A, alkylsulfonate and ligninsulfonate were thoroughly mixed and pulverized with a pin mill so that a powder was formed.

Further, the above-mentioned amount of screened Shirasu Ballon was given into a pan coater and the above-mentioned amount of spindle oil was dropwise added thereto at room temperature. After the spindle oil was adequately dispersed, the above-mentioned powder was gradually added to the pre-treated core material in the pan coater at room temperature. The coating apparatus was then operated at room temperature until visual inspection showed that the core material was uniformly covered with powder.

Example 2

The compounds and quantities used were as follows:

| | |
|---|---|
| Compound A | 10.0% by weight |
| Alkylnaphthalenesulfonate | 1.0% by weight |
| Dialkylsulfosuccinate | 4.0% by weight |
| Ligninsulfonate | 6.0% by weight |
| Spindle oil | 14.0% by weight |
| Shirasu Ballon | 65.0% by weight. |

In order to adjust the particle size of the core material, Shirasu Ballon was screened with sieves, which were similar to Japanese Industrial Standard sieves and hat openings of a diameter of 500 μm and 1,400 μm respectively.

The above mentioned amounts of Compound A, alkylnaphthalenesulfonate, dialkylsulfosuccinate and ligninsulfonate were thoroughly mixed and pulverized with a pin mill so that a powder was formed. The agrochemical formulation was then prepared in the same manner as described in Example 1.

Fifty grams of the resulting formulation were put into a bag (12×12 cm) of a water-soluble poly(vinyl alcohol) film having a thickness of 40 μm. The bag had been prepared by using a heat sealer, and after the bag was filled, it was sealed by means of a heat sealer.

Example 3

The compounds and quantities used were as follows:

| | |
|---|---|
| Compound B | 3.0% by weight |
| Alkylnaphthalenesulfonate | 1.0% by weight |
| Dialkylsulfosuccinate | 4.0% by weight |
| Ligninsulfonate | 6.0% by weight |
| Spindle oil | 14.0% by weight |
| Shirasu Ballon | 72.0% by weight |

The agrochemical formulation was prepared in the same manner as described in Example 1. Fifty grams of said formulation were then sealed in a water-soluble bag as described in Example 2.

COMPARISON EXAMPLES

Example I

The compounds and quantities used were as follows:

| | |
|---|---|
| Compound A | 10.0% by weight |
| Spindle oil | 2.0% by weight |
| Calcined perlite | 88.0% by weight |

Calcined perlite was infiltrated with spindle oil in the above-mentioned ratio in a pan coater at room temperature. The resulting core material was then coated with the above-mentioned amount of Compound A by operating the pan coater at room temperature. Fifty grams of the obtained formulation were then sealed in a water-soluble bag as described in Example 2.

Example II

The compounds and quantities used were as follows:

| | |
|---|---|
| Compound A | 10.0% by weight |
| Sodium alkylbenzenesulfonate | 0.5% by weight |
| Bentonite powder | 30.0% by weight |
| Clay powder | 59.5% by weight |

After the above-mentioned components were thoroughly mixed in the above-mentioned amounts at room temperature, water was added and the mixture was kneaded until a pasty product was formed. The pasty mixture was then subjected to extrusion molding using an extruder followed by drying in a fluidized bed of a drier. The particle size was then adjusted in the same manner as described in Example 1.

USE EXAMPLES

Example A

Test for dispersion properties

As shown in FIG. 1, seven bottles each having a diameter of about 7.5 cm were arranged as obstacles in a pool made of concrete, which was 4.1 m long and 2.6 m broad. 500 liters of water were then poured into the pool to cause a depth of water of 5 cm. A water-soluble package of 6.0 g of the sealed formulations described in Examples 2 and I respectively was separately tested by throwing in each case the sealed package into the pool. Thereafter, a fixed amount of water was collected at time intervals from each point shown in FIG. 1. The concentration of the biologically active compound was measured in each sample of water collected, in order to determine the dispersion state. The results are shown in Table 1. The numerical values of the concentrations in this Table are exressed in ppm.

TABLE 1

| | Collecting point | | | | | |
|---|---|---|---|---|---|---|
| | 1 | | 2 | | 3 | |
| Elapsed | Concentration of active compound | | | | | |
| time (min) | Example 2 | Example I | Example 2 | Example I | Example 2 | Example I |
| 0 | 0 | 0 | 0 | 0 | 0 | 0 |
| 10 | 0.63 | 1.68 | 0.04 | 0.10 | 0.02 | 0 |
| 20 | 1.71 | 1.03 | 0.21 | 0.28 | 0.10 | 0 |
| 30 | 1.49 | 1.11 | 0.81 | 0.31 | 0.32 | 0.04 |
| 60 | 1.21 | 1.16 | 1.00 | 0.32 | 0.73 | 0.04 |
| 120 | 1.13 | 1.25 | 1.07 | 0.58 | 0.82 | 0.05 |
| 240 | 1.09 | 1.01 | 1.02 | 0.35 | 0.85 | 0.14 |

Example B

Test for dispersion properties

The test was conducted in the same manner as the test described in Example A. However, the formulations of Examples 2 and II were used in this case.

The results are shown in Table 2. The numerical values of the concentrations in this table are expressed in ppm.

TABLE 2

| Elapsed time (min) | Collecting point | | | | | |
|---|---|---|---|---|---|---|
| | 2 | | 6 | | 5 | |
| | Concentration of active compound | | | | | |
| | Example 2 | Example II | Example 2 | Example II | Example 2 | Example II |
| 0 | 0 | 0 | 0 | 0 | 0 | 0 |
| 10 | 0.13 | 0.31 | 0.44 | 0.21 | 0 | 0.16 |
| 20 | 0.38 | 0.13 | 0.73 | 0.23 | 0.32 | 0.16 |
| 30 | 0.72 | 0.14 | 0.82 | 0.32 | 0.64 | 0.14 |
| 60 | 0.91 | 0.19 | 0.97 | 0.37 | 1.08 | 0.16 |
| 120 | 1.13 | 0.82 | 1.08 | 0.65 | 1.02 | 0.15 |
| 240 | 1.11 | 0.86 | 1.14 | 0.66 | 1.02 | 0.28 |

The data in Tables A and B show that the formulations according to the invention are extremely speedily and uniformly dispersed on the surface of water of a paddy field. Further, no phytotoxicity is observed and a sufficient degree of activity is also achieved.

Since the formulations according to the invention exhibit very good spreading properties, it is not necessary to throw the formulations always into the centre of a paddy field when applying the formulation. It is rather possible to achieve a dispersion over the entire surface of a paddy field, even if the formulation is applied to the paddy field in the vicinity of a footpath.

The letter

Figure 1:
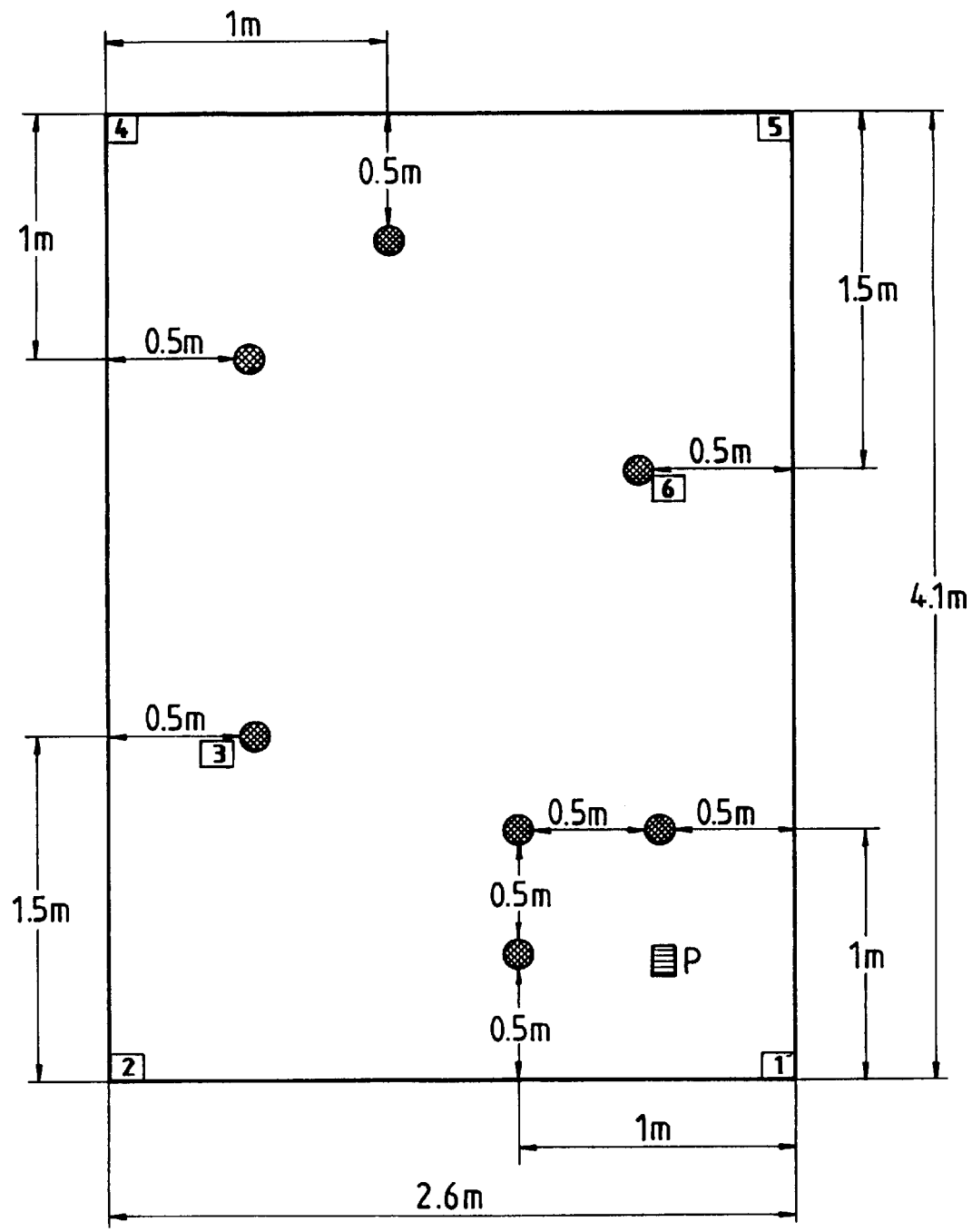
FIG. 1 is a schematic view on a pool used for testing the dispersion properties of the formulations described in Examples A and B.

P indicates the point at which each of the formulations was thrown into the pool.

The numbers (1) to (6) indicate the points at which water was collected.

The circles (#) indicate the location of the obstades, i.e. bottles having in each case a volume of 500 ml.

We claim:

1. An agrochemical formulation in the form of solid particles consisting essentially of
   A) at least one solid core material having an apparent specific density of less than 1 and a particle diameter within the range from about 500 μm to about 1,400 μm, wherein the core material is selected from the group consisting of pumice, calcined perlite, processed shirasu, calcined obsidian, calcined pumice and vermiculite, and
   B) a coating layer comprising
      at least one biologically active compound,
      at least one substance having the ability to reduce the interfacial tension between water and air selected from the group consisting of alkylbenzenesulfonates, alkylsulfates, alkylnaphthalenesulfonates, alkylphosphoric esters, polyoxyethylene alkyl ethers, glycerin fatty acid esters, sorbitan fatty acid esters, dialkylsulfosuccinates, ligninsulfonate, condensates of naphthalenesulfonate and formalin, alkylammonium salts, alkylglycine salts, alanine salts, siliconpolyether surfactants, alkylallylsulfonate and a camphor, and spindle oil.

2. An agrochemical formulation according to claim 1, wherein the biologically active compound is selected from the group consisting of insecticidal compounds, fungicidal compounds, nematocidal compounds, herbicidal compounds, plant nutritive substances and plant growth regulants.

3. An agrochemical formulation according to claim 1 comprising at least one additive selected from extenders, stabilizers and colorants.

4. An agrochemical formulation according to claim 1, wherein said biologically active compound is a herbicidal compound.

5. An agrochemical formulation according to claim 1, wherein said biologically active compound is at least one compound selected from the group consisting of
2-benzothiazol-2-yloxy-N-methylacetanilide,
2-isopropoxyphenyl-N-methylcarbamate,
1-(6-chloro-3-pyridylmethyl)-N-nitro-imidazolidin-2-ylideneamine,
O,O-dimethyl-O-[3-methyl-4-(methylthio)-phenyl]-thiophosphate,
1-(4-chlorophenoxy)-3,3-dimethyl-1-(1,2,4-triazol-1-yl)-2-butanone,
all-rac-1-(biphenyl-4-yloxy)-3,3-dimethyl-1- (1H- 1,2,4-triazol- 1-yl)-butan-2-ol,
zinc propylenebisdithiocarbamate,
(RS)-2-bromo-N-(α,α-dimethylbenzyl)-3,3-dimethyl-butyramide,
2-chloro-2',6'-diethyl-N-(2-propoxyethyl)- acetanilide,
2-chloro-2',6'-diethyl-N-(2-butoxymethyl)- acetanilide,
2-chloro-N-(3-methoxy-2-thenyl)-2',6'-dimethylacetanilide,
S-(4-chlorobenzyl)-N,N-diethylthiocarbamate,
S-benzyl 1,2-dimethylpropyl(ethyl)thio-carbamate,
O-3-tert-butylphenyl 6-methoxy-2-pyridyl- (methyl) thiocarbamate,
S-ethylhexamido-1H-azepin-1-carbothioate,
1-(diethylcarbamoyl)-3-(2,4,6-trimethyl-phenyl- sulfonyl)-1,2,4-thiazole,
1-(3-chloro-4-trifluoromethylphenyl)-4-(N,N-dimethylcarbamoyl)-5(4H)-tetrazolinone,
1-(3-chloro-4-trifluoromethylthio-phenyl)-4-(N,N-dipropyl carbamoyl)-5(4H)-tetrazolinone,
1-(3-chloro-4-trifluoromethoxy-phenyl)-4-(N,N-dipropylcarbamoyl)-5(4H)-tetrazolinone,
1-(3-chloro-4-isopropylphenyl)-4-(N,N-diethyl-carbamoyl)-5(4H)-tetrazolinone,
1-(3-chloro-4-isopropylphenyl)-4-(N,N-dipropylcarbamoyl)-5(4H)-tetrazolinone,
1-(3-chloro-4-isopropylphenyl)-4-(N,N-diallyl-carbamoyl)-5(4H)-tetrazolinone,
1-(2-chlorophenyl)-4-(N,N-diethylcarbamoyl)-5(4H)-tetrazolinone,
1-(2-chlorophenyl)-4-(N,N-dipropylcarbamoyl)-5(4H)-tetrazolinone,
1-(2-chloro-6-methylphenyl)-4-(N,N-diethyl- carbamoyl)-5 (4H)-tetrazolinone,
1-(2,6-dichlorophenyl)-4-(N,N-diethylcarbamoyl)-5(4H)-tetrazolinone,
1-(2-chloro-6-methylphenyl)-4-(N-ethyl-N-iso-propyl)-5 (4H)-tetrazolinone,
1-(2-chloro-6-methylphenyl)-4-(N,N-dipropyl-carbamoyl)-5(4H)-tetrazolinone,
1-(2-chlorophenyl)-4-(N-cyclopentyl-N-ethyl- carbamoyl)-5(4H)-tetrazolinone,
1-(2-chlorophenyl)-4-(N-cyclopentyl-N-propyl-carbamoyl)-5(4H)-tetrazolinone, 1-(2-chlorophenyl)-4-(N-cyclohexyl-N-ethyl-carbamoyl)-5 (4H)-tetrazolinone,
1-(2-chloro-6-methylphenyl)-4-(N-cyclopentyl-N-propylcarbamoyl)-5(4H)-tetrazolinone,
1-(2-bromophenyl)-4-(N-cyclopentyl-N-ethyl- carbamoyl)- 5(4H)-tetrazolinone,
1-(2-bromophenyl)-4-(N-cyclopentyl-N-propyl- carbamoyl) -5(4H)-tetrazolinone,
1-(2-bromo-6-methylphenyl)-4-(N-cyclopentyl-N-propylcarbamoyl)-5(4H)-tetrazolinone,
methyl 2-[(4,6-dimethoxy-2-pyrimidinyl)-oxy]- 6-[1-(methoxyimino)-ethyl]-benzoate,
methyl α-(4,6-dimethoxypyrimidin-2-ylcarbamoylsulfamoyl)-O-toluate,
ethyl-5-(4,6-dimethoxypyrimidin-2-yl-carbamoyl sulfamoyl)- 1-methylpyrazol-4-carboxylate,
N-(2-chloroimidazol [1,2-a]pyridin-3-yl-sulfonyl)-N'-(4,6-dimethoxy-2-pyrimidyl)urea,
N-((4,6-dimethoxypyrimi din-2-yl)-aminocarbonyl)-1-methyl-4-(2-methyl-2H-tetrazol-5-yl)-1H-pyrazol-5-sulfonamide,
N-[[4,6-dimethoxy-1,3,5-triazin-2-yl)-amino]-carbonyl]-2-(2-methoxyethoxy)benzenesulfonamide,
1-[[o-(cyclopropylcarbonyl)phenyl]-sulfamoyl-3-(4,6-dimethoxy-2-pyrimidinyl)urea,
4-(2,4-dichlorobenzoyl)-1,3-dimethylpyrazol-5- yl-p-toluenesulfonate,
2-[4-(2,4-dichloro-m-toluyl)-1,3-dimethyl-pyrazol-5-yloxy]-4-methylacetophenone,
2-[4-(2,4-dichlorobenzoyl)-1,3-dimethylpyrazol-5-yloxy]-acetophenone,
2-(β-naphthyloxy)-propionanilide,
(RS)-2-(2,4-dichloro-m-tolyloxy)-propion-anilide,
n-butyl (R)-2-[4-(2-fluoro-4-cyanophenoxy)- phenoxy]-propionate,
1-(α,α-dimethylbenzyl)-3-p-tolylurea,
N-[(2-chlorophenyl)-methyl]-N'-(1-methyl-1- phenylethyl)-urea,
2-methyl-4-chlorophenoxybutyric acid,
2,4-dichlorophenoxyacetic acid,
2,4-bis-(ethylamino)-6-methylthio-1,3,5-triazine,
2-ethyl amino-4-(1,2-dimethylpropylamino)-6- methylthio-1,3,5-triazine.
6. An agrochemical formulation according to claim 1, wherein said biologically active compound is at least one of 2-benzothiazol-2-yloxy-N-methylacetanilide or 1-(2-chlorophenyl)-4-(N-cyclohexyl-N-ethylcarbamoyl)-5(4H)-tetrazolinone.
7. A method for applying agrochemicals to the water of paddy fields, which method comprises adding to the water surface of paddy fields a formulation in the form of solid particles consisting essentially of
A) at least one solid core material having an apparent specific density of less than 1 and a particle diameter within the range from about 500 μm to about 1,400 μm, wherein the core material is selected from the group consisting of pumice, calcined perlite, processed shirasu, calcined obsidian, calcined pumice and vermiculite, and
B) a coating layer comprising
at least one biologically active compound,
at least one substance having the ability to reduce the interfacial tension between water and air selected from the group consisting of alkylbenzenesulfonates, alkylsulfates, alkylnaphthalenesulfonates, alkylphosphoric esters, polyoxyethylene alkyl ethers, glycerin fatty acid esters, sorbitan fatty acid esters, dialkylsulfosuccinates, ligninsulfonate, condensates of naphthalenesulfonate and formalin, alkylammonium salts, alkylglycine salts, alanine salts, siliconpolyether surfactants, alkylallylsufonates and a camphor, and spindle oil.
8. A method according to claim 7, wherein the biologically active compound is selected from the group consisting of insecticidal compounds, fungicidal compounds, nematocidal compounds, herbicidal compounds, plant nutritive substances and plant growth regulantes.
9. A method according to claim 7, wherein said biologically active compound is a herbicidal compound.
10. A method according to claim 7, comprising at least one additive selected from extenders, stabilizers and colorants.
11. A method according to claim 7, wherein said biologically active compound is at least one compound selected from the group consisting of
2-benzothiazol-2-yloxy-N-methylacetanilide,
2-isopropoxyphenyl-N-methylcarbamate,
1-(6-chloro-3-pyridylmethyl)-N-nitro-imidazolidin-2-ylideneamine,
O,O-dimethyl-O-[3-methyl-4-(methylthio)-phenyl]-thiophosphate,
1-(4-chlorophenoxy)-3,3-dimethyl- 1-(1,2,4- triazol-1-yl)-2-butanone,
all-rac- 1-(biphenyl-4-yloxy)-3,3-dimethyl-1-(1H-1,2,4-triazol- 1-yl)-butan-2-ol,
zinc propylenebisdithiocarbamate,
(RS)-2-bromo-N-(α,α-dimethylbenzyl)3,3- dimethyl-butyramide,
2-chloro-2',6'-diethyl-N-(2-propoxyethyl)- acetanilide,
2-chloro-2',6'-diethyl-N-(2-butoxymethyl)- acetanilide,
2-chloro-N-(3-methoxy-2-thenyl)-2',6'-dimethylacetanilide,
S-(4-chlorobenzyl)-N,N-diethylthiocarbamate,
S-benzyl 1,2-dimethylpropyl(ethyl)thio-carbamate,
O-3-tert-butylphenyl 6-methoxy-2-pyridyl-(methyl) thiocarbamate,
S-ethylhexamido-1H-azepin- 1-carbothioate,
1-(diethylcarbamoyl)-3-(2,4,6-trimethyl-phenyl-sulfonyl)-1,2,4-thiazole,
1-(3-chloro-4-trifluoromethylphenyl)-4-(N,N-dimethylcarbamoyl)-5(4H)-tetrazolinone,
1-(3-chloro-4-tri fluoromethylthio-phenyl)-4-(N,N-dipropylcarbamoyl)-5(4H)-tetrazolinone,
1-(3-chloro-4-trifluoromethoxy-phenyl)-4-(N,N-dipropylcarbamoyl)-5(4H)-tetrazolinone,
1-(3-chloro-4-isopropylphenyl)-4-(N,N-diethyl- carbamoyl)-5(4H)-tetrazolinone,
1-(3-chloro-4-isopropylphenyl)-4-(N,N-dipropylcarbamoyl)-5(4H)-tetrazolinone,
1-(3-chloro-4-isopropylphenyl)-4-(N,N-diallyl- carbamoyl)-5(4H)-tetrazolinone,
1-(2-chlorophenyl)-4-(N,N-diethylcarbamoyl)-5(4H)-tetrazolinone,
1-(2-chlorophenyl)-4-(N,N-dipropylcarbamoyl)-5(4H)-tetrazolinone,
1-(2-chloro-6-methylphenyl)-4-(N,N-diethyl- carbamoyl)-5(4H)-tetrazolinone,
1-(2,6-dichlorophenyl)-4-(N,N-diethylcarbamoyl)-5(4H)-tetrazolinone,
1-(2-chloro-6-methylphenyl)-4-(N-ethyl-N-iso-propyl)-5(4H)-tetrazolinone,
1-(2-chloro-6-methylphenyl)-4-(N,N-dipropyl-carbamoyl)-5(4H)-tetrazolinone,
1-(2-chlorophenyl)-4-(N-cyclopentyl-N-ethyl- carbamoyl)-5(4H)-tetrazolinone, 1-(2-chlorophenyl)-4-(N-cyclopentyl-N-propyl- carbamoyl)-5(4H)-tetrazolinone,
1-(2-chlorophenyl)-4-(N-cyclohexyl-N-ethyl-carbamoyl)-5(4H)-tetrazolinone,
1-(2-chloro-6-methylphenyl)-4-(N-cyclopentyl-N-propylcarbamoyl)-5(4H)-tetrazolinone,
1-(2-bromophenyl)-4-(N-cyclopentyl-N-ethyl- carbamoyl)-5(4H)-tetrazolinone,
1-(2-bromophenyl)-4-(N-cyclopentyl-N-propyl- carbamoyl)-5(4H)-tetrazolinone,
1-(2-bromo-6-methylphenyl)-4-(N-cyclopentyl-N-propylcarbamoyl)-5(4H)tetrazolinone,
methyl 2-[(4,6-dimethoxy-2-pyrimidinyl)-oxy]- 6-[1-(methoxyimino)-ethyl]-benzoate,
methyl α-(4,6-dimethoxypyrimidin-2-ylcarbamoylsulfamoyl)-O-toluate,
ethyl-5-(4,6-dimethoxypyrimidin-2-yl-carbamoylsulfamoyl)- 1-methylpyrazol-4-carboxylate,
N-(2-chloroimidazol [1,2-a]pyridin-3-yl-sulfonyl)-N'-(4,6-dim ethoxy-2-pyrimidyl)urea,
N-((4,6-dimethoxypyrimi din-2-yl)-aminocarbonyl)-1-methyl-4-(2-methyl -2H-tetrazol-5-yl)--1H-pyrazol-5-sulfonamide,
N-[[4,6-dimethoxy-1,3,5-triazin-2-yl)-amino]-carbonyl]-2-(2-methoxyethoxy)benzenesulfonamide,
1-[[o-(cyclopropylcarbonyl)phenyl]-sulfamoyl-3-(4,6-dimethoxy-2-pyrimidinyl)urea,
4-(2,4-dichlorobenzoyl)-1,3-dimethylpyrazol-5-yl-p-toluenesulfonate,
2-[4-(2,4-dichloro-m-toluyl)-1,3-dimethyl-pyrazol-5-yloxy]-4-methylacetophenone,
2-[4-(2,4-dichlorobenzoyl)-1,3-dimethylpyrazol-5-yloxy]-acetophenone,
2-(β-naphthyloxy)-propionanilide,
(RS)-2-(2,4-dichloro-m-tolyloxy)-propion-anilide,
n-butyl (R)-2-[4-(2-fluoro-4-cyanophenoxy)- phenoxy]-propionate,
1-(α,α-dimethylbenzyl)-3-p-tolylurea,
N-[(2-chlorophenyl)-methyl]-N'-(1-methyl-1- phenylethyl)-urea,
2-methyl-4-chlorophenoxybutyric acid,
2,4-dichlorophenoxyacetic acid,
2,4-bis-(ethylamino)-6-methylthio-1,3,5-triazine,
2-ethyl amino-4-(1,2-dimethylpropylamino)-6- methylthio-1,3,5-triazine.

12. A method according to claim 7, wherein said biologically active compound is at least one of 2-benzothiazol-2-yloxy-N-methylacetanilide or 1-(2-chloro-phenyl)4-(Ncyclohexyl-N-ethylcarbamoyl)-5(4H)-tetrazolinone.

* * * * *